(12) United States Patent
Arad et al.

(10) Patent No.: US 7,592,459 B2
(45) Date of Patent: Sep. 22, 2009

(54) USE OF PURIFIED DONEPEZIL MALEATE FOR PREPARING PHARMACEUTICALLY PURE AMORPHOUS DONEPEZIL HYDROCHLORIDE

(75) Inventors: Oded Arad, Rechovot (IL); Lior Zelikovitch, Mazkeret Batia (IL); Mohammed Alnabari, Hura (IL); Michael Brand, RaAnana (IL); Irina Gribun, Bat-Yam (IL); Ada Salman, Ramat-Gan (IL); Meital Shiffer, Tel Aviv (IL); Moty Shookrun, Petach-Tikva (IL); Orna Kurlat, Beer-Sheba (IL); Moshe Bentolila, Moshav Tkuma (IL); Joseph Kaspi, Givatayim (IL)

(73) Assignee: Chemagis Ltd., Bnei-Brak (IL)

( * ) Notice: Subject to any disclaimer, the term of this patent is extended or adjusted under 35 U.S.C. 154(b) by 518 days.

(21) Appl. No.: 11/235,106

(22) Filed: Sep. 27, 2005

(65) Prior Publication Data

US 2006/0069125 A1 Mar. 30, 2006

Related U.S. Application Data

(60) Provisional application No. 60/613,707, filed on Sep. 29, 2004.

(51) Int. Cl.
*C07D 211/02* (2006.01)
(52) U.S. Cl. .................. 546/206; 546/205; 514/319
(58) Field of Classification Search .................. 514/319; 546/205, 206
See application file for complete search history.

(56) References Cited

U.S. PATENT DOCUMENTS

| | | | |
|---|---|---|---|
| 4,895,841 A | 1/1990 | Sugimoto et al. | |
| 5,606,064 A | 2/1997 | Lensky | |
| 5,900,425 A | 5/1999 | Kanikanti et al. | |
| 5,985,864 A | 11/1999 | Imai et al. | |
| 6,140,321 A | 10/2000 | Imai et al. | |
| 6,245,911 B1 | 6/2001 | Imai et al. | |
| 6,252,081 B1 | 6/2001 | Iimura et al. | |
| 6,372,760 B1 * | 4/2002 | Kato et al. ................ | 514/319 |
| 6,734,195 B2 | 5/2004 | Weisman et al. | |
| 6,844,440 B2 | 1/2005 | Lerman et al. | |
| 6,953,856 B2 * | 10/2005 | Radhakrishnan et al. .... | 546/185 |
| 7,186,742 B2 * | 3/2007 | Dombroski et al. ......... | 514/406 |
| 2002/0142050 A1 | 10/2002 | Straub et al. | |
| 2004/0034057 A1 | 2/2004 | Imai et al. | |
| 2004/0048893 A1 | 3/2004 | Lerman et al. | |
| 2004/0229914 A1 | 11/2004 | Reddy et al. | |
| 2005/0107613 A1 | 5/2005 | Tarur et al. | |
| 2005/0142190 A1 | 6/2005 | Adin et al. | |
| 2006/0061125 A1 | 3/2006 | Schmidt et al. | |
| 2008/0076928 A1 | 3/2008 | Tarur et al. | |

FOREIGN PATENT DOCUMENTS

| | | |
|---|---|---|
| EP | 296560 B1 | 2/1996 |
| EP | 0 740 934 A1 | 11/1996 |
| EP | 711756 B1 | 7/1998 |
| EP | 1 027 887 A2 | 8/2000 |
| EP | 1 120 109 A2 | 8/2001 |
| EP | 1386607 | 4/2004 |
| WO | WO 97/22584 | 6/1997 |
| WO | WO 97/22584 A1 | 6/1997 |
| WO | WO 99/36405 A1 | 7/1999 |
| WO | WO 03/048135 A1 | 6/2003 |
| WO | WO 2004/000317 A1 | 12/2003 |
| WO | WO 2004/016589 | 2/2004 |
| WO | WO 2004/039352 A2 | 5/2004 |
| WO | WO 2004/087660 | 10/2004 |
| WO | WO 2004/099142 | 11/2004 |
| WO | WO2006/015338 * | 2/2006 |
| WO | WO2006/030249 * | 3/2006 |

OTHER PUBLICATIONS

Doser et al. CA144:357714 (2006) RN 881405-87-4; RN 881405-89-6; RN 881405-91-0.*
Kumar et al. CA141:428014 (2004) RN 79512-61-1.*
Mezei et al. CA144:318583 (2006) RN 880085-01-8.*
Brittain H G "Polymorphism in pharmaceutical solids" p. 208-218 (1999).*
Lieberman et al. "Pharmaceutical dosage forms" p. 462-465 (1989).*
Berge "Pharmaceutical salts" J. Pharm. sci. 66(1) p. 1-19 (1977).*
Berge et al. "Pharmaceutical Salts", J. Pharmaceut. Sciences, vol. 66, No. 1, pp. 1-19, (1977).
Miro et al "Physiocochemical and Pharmacological Properties of Nimesulide/β-cyclodextrin Formulations", Database CAPSULS on STN (Columbus, OH, USA), No. 133:406394—S.T.P. Pharm Sciences, 10(2) 157-164 (2000).
Bryson et al., "ADIS New Drug Profile: Donepezil", *Drugs & Aging*, 10(3), 234-239 (1997).
Sebhatu et al., "Relationships between the effective interparticulate contact area and the tensile strength of tablets of amorphous and crystalline lactose of varying particle size", European J Pharma Science, vol. 6, pp. 235-242 (1999).

* cited by examiner

*Primary Examiner*—Celia Chang
(74) *Attorney, Agent, or Firm*—Leydig, Voit & Mayer, Ltd.

(57) ABSTRACT

The present invention provides a crystalline donepezil maleate, which is used as an intermediate in the preparation of donepezil hydrochloride. Also provided are novel processes for producing same in substantially pure form and a process for producing pharmaceutically pure amorphous donepezil hydrochloride therefrom.

7 Claims, No Drawings

USE OF PURIFIED DONEPEZIL MALEATE FOR PREPARING PHARMACEUTICALLY PURE AMORPHOUS DONEPEZIL HYDROCHLORIDE

RELATED APPLICATIONS

The present application claims priority from U.S. Provisional Patent Application No. 60/613,707 filed on Sep. 29, 2004, which is incorporated herein by reference.

FIELD OF THE INVENTION

The present invention relates to the maleate salt of 1-benzyl-4-[(5,6-dimethoxy-1-indanon)-2-yl)methyl]piperidine, commonly known as donepezil, and processes for its preparation and use.

BACKGROUND OF THE INVENTION

Donepezil hydrochloride (I) is a reversible acetylcholinesterase inhibitor that has the following structure:

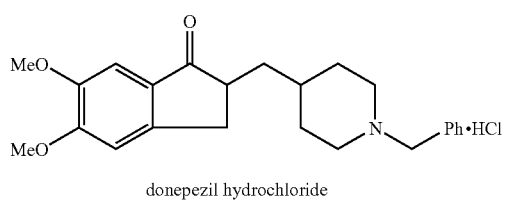

donepezil hydrochloride

Donepezil (known as 1-benzyl-4-[(5,6-dimethoxy-1-indanon-2-yl)methyl]piperidine)hydrochloride is an effective drug for treating dementia and Alzheimer's disease. The drug is administrated in the form of oral solid formulations such as 5 and 10 mg film coated tablets, capsules and granules and is given to the patients once daily.

The preparation of donepezil was described in several patents, for example: U.S. Pat. Nos. 4,895,841, 6,252,081, PCT Patent Application published as WO 97/22584, EP Patent 1386607 and others.

U.S. Pat. Nos. 5,985,864, 6,140,321, 6,245,911, U.S patent applications Publication Nos. 2004/0034057 and 2004/0229914, PCT Patent Application published as WO 2004/087660, and an article published in Indian Journal of Chemistry, Section B: Organic Chemistry including Medicinal Chemistry 44B(6), 1231-1235, 2005, which are incorporated by reference as if fully set forth herein, describe various amorphous and crystalline forms of donepezil hydrochloride U.S. Pat. Nos. 5,985,864 and 6,140,321 describe five different crystalline forms of donepezil hydrochloride (including hydrates) as well as an amorphous donepezil hydrochloride. The different crystalline forms of donepezil hydrochloride described in these patents, may be prepared either by dissolving the salt in a polar solvent (such as methanol), while heating, and adding a less polar solvent (such as isopropyl ether) upon cooling, followed by filtration of the separated crystals, or by dissolving the base in a polar solvent (such as methanol) while heating and adding an alcoholic solution of concentrated hydrochloric acid followed by filtration of the separated crystals.

U.S. Pat. No. 6,245,911 describes three novel crystalline forms of donepezil hydrochloride (A, B and C) and the processes for their preparation.

US Patent Application Publication No. 2004/0034057 discloses a process for industrial production of a crystalline form of donepezil hydrochloride.

US Patent Application Publication No. 2004/0229914 discloses a novel crystalline form VI of donepezil hydrochloride and process for preparing of same.

US Patent Application Publication No. 2005/0107613 discloses three crystalline oxalate salts of donepezil and methods of their preparation.

PCT Patent Application published as WO 2004/099142 discloses crystalline forms of the hydrobromide salt of donepezil and processes for their preparation.

The detailed prior art shows that donepezil hydrochloride tends to appear in more than one crystalline form, each having different characteristic behavior. These different crystalline forms are known as polymorphs. While polymorphs have the same chemical composition, they differ in packing and geometrical arrangement, and exhibit different physical properties such as melting point, shape, color, hardness, bulk density, deformability, stability, dissolution, and the like.

Since each polymorph has different characteristic behavior, a major problem of using a crystalline polymorphic drug is associated with obtaining a reproducible solid form of the active pharmaceutical ingredient. An example of the limitations associated with polymorphs is the anti-epilepsy drug carbamazepine, in which only a specific crystalline form is allowed, because the US Pharmacopoeia dictates in the monograph the pharmaceutical use of only a specific crystalline form (characterized by its X-ray diffraction pattern). In addition, other health authorities require assurance for the correct crystalline form of the drug used as well.

One way of alleviating the problem, of obtaining reproducible solid forms of active pharmaceutical ingredients, is to use non-crystalline forms of these materials. On one hand the problem of having variety of crystalline forms does not exist. On the other hand, non-crystalline amorphous solids are known to have better dissolution. As a result one can expect a good, consistent availability of the active ingredient. Therefore, non-crystalline materials may be offered as a solution to this problem because when a material is amorphous, there cannot be polymorphism.

Normally such a non-crystalline form has a better solubility and faster dissolution rate, thus assuring good bioavailability.

The use of stable amorphous donepezil hydrochloride in pharmaceutical preparations is provided in U.S. Pat. No. 6,734,195 (to the present applicant). Stable pharmaceutical preparations containing amorphous donepezil hydrochloride are easily obtained according to the teachings of this application. In addition there is no change in the impurity content of the amorphous material stored at 40° C. after 3 and 6 months of storage at 75% relative humidity, and the highest impurity level is 0.1% with the total impurities level of 0.4%. These levels are exactly the initial values. There was no indication of chemical degradation of amorphous donepezil hydrochloride produced.

Another problem concerned with using crystalline donepezil is that the purification of the compound either by crystallizing the base or the hydrochloride salt, as taught in the literature, may require several crystallization steps to yield a pharmaceutically pure product and hence the process suffers from relatively low yields.

Since the existing crystallization methods of donepezil base and donepezil hydrochloride suffer from relatively low yields and unstable polymorphism, there is a recognizable need for a simple and efficient purifying process for obtaining a stable, amorphous donepezil hydrochloride in pharmaceutical grade purity. On the other hand, the crystallization of donepezil maleate proceeds with much better yields and affords better and consistent quality.

Thus, the present invention provides a process for obtaining pharmaceutically pure amorphous donepezil hydrochloride via crystallization of highly pure crude donepezil maleate, which yields pharmaceutically pure amorphous donepezil hydrochloride.

SUMMARY OF THE INVENTION

The present invention provides a cheap, efficient and straightforward process for obtaining substantially pure amorphous donepezil hydrochloride.

According to a preferred embodiment of the present invention, donepezil maleate is produced by converting the donepezil free base, which may be obtained, for example, as described in EP Patent Application No. 1386607 (to the present applicant), to donepezil maleate, which is easily precipitated in high purity and yield.

According to one embodiment of the present invention, donepezil maleate may be crystallized from an organic solvent to obtain a highly pure product.

According to another preferred embodiment of the present invention, there is provided a novel process for converting donepezil maleate to an amorphous pharmaceutically pure donepezil hydrochloride, suitable for use in preparation of dosage forms, using freeze-drying or spray-drying techniques.

DESCRIPTION OF THE PREFERRED EMBODIMENTS

The present invention is based on the surprising finding that it is not necessary to use repeated crystallizations to obtain highly pure donepezil hydrochloride and that by converting donepezil maleate (optionally purified by crystallization) to donepezil hydrochloride, a highly pure product is obtained.

According to one aspect of the present invention donepezil base used in the process for preparing donepezil maleate, may be obtained by any of the donepezil synthetic processes including the one described in European patent application 1386607.

According to one embodiment of the present invention donepezil base, obtained by any of the known processes as a reaction mixture, is isolated by the process of the present invention by adding maleic acid and isolating the precipitated product as donepezil maleate.

According to another aspect of the present invention donepezil base, dissolved in toluene, is treated with aqueous solution of maleic acid and the resulting maleate salt precipitates selectively as donepezil maleate. The salt is insoluble in the aqueous medium as well as in toluene and therefore the precipitation is selective in addition to being almost quantitative, while most of the impurities are left either in the aqueous or in the organic phase.

According to yet another aspect of the present invention, donepezil maleate is isolated and consequently crystallized.

According to another embodiment of the present invention the process for obtaining donepezil maleate comprises the steps of:

a) providing a solution of donepezil base in an organic solvent;

b) adding maleic acid and precipitating crude donepezil reaction product as donepezil maleate;

c) cooling the reaction product and separating the obtained solid; and d) optionally washing the solid with water and a second organic solvent and isolating the product.

According to yet another aspect of the present invention, the organic solvent used for dissolving donepezil base may be selected from the group consisting of dichloromethane, chloroform, ethyl acetate, isopropyl acetate, isobutyl acetate, xylenes, and toluene, or a mixture thereof, preferably the solvent is toluene.

According to yet another aspect of the present invention the technique for separating the obtained solid is selected from the group consisting of filtration, vacuum filtration, decantation and centrifugation, preferably filtration or centrifugation.

According to yet another aspect of the present invention, the second organic solvent used for washing donepezil maleate may be selected from the group consisting of acetone, diethyl ether, diisopropyl ether, diisobutyl ether, methyl tert-butyl ether, hexane, or any mixture thereof, preferably acetone.

According to yet another embodiment of the present invention, donepezil maleate may be crystallized from an organic solvent to obtain a highly pure product. The process comprises the steps of:

a) dissolving donepezil maleate in an organic solvent, optionally at reflux conditions;

b) cooling and mixing to afford crystals; and c) filtering the obtained solid and washing.

According to one aspect of the present invention, the solvent for crystallizing donepezil maleate may be selected from the group consisting of acetonitrile, methanol, ethanol, n-propanol, isopropanol, n-butanol, sec-butanol, acetone, methylethyl ketone, diethyl ketone, methylpropyl ketone methylisopropyl ketone or a mixture thereof, preferably acetone.

According to yet another aspect of the present invention, crystallized donepezil maleate may be obtained having a purity greater than 99.5% and preferably equal to or greater than 99.9%.

According to yet another aspect of the present invention, by using the process provided herein, donepezil maleate may be readily converted to donepezil hydrochloride without formation of any impurities and consequently used in pharmaceutical dosage forms.

According to yet another embodiment of the present invention the process for converting donepezil maleate to amorphous donepezil hydrochloride comprises the steps of:

a) suspending pure donepezil maleate in a mixture of an organic solvent and water;

b) adding aqueous inorganic base;

c) extracting and separating the phases;

d) washing the organic phase with water and separating the phases;

e) adding equimolar quantity of aqueous hydrochloric acid to the organic phase and separating the phases (donepezil hydrochloride is freely soluble in water);

f) optionally adding an inactive pharmaceutical ingredient to the aqueous phase and stirring to dissolution; and g) evaporating the water by freeze drying or spray drying.

According to yet another aspect of the present invention the organic solvent may be selected from the group consisting of dichloromethane, chloroform, ethyl acetate, isopropyl acetate, isobutyl acetate, xylenes and toluene, or a mixture thereof, preferably the solvent is toluene.

According to yet another aspect of the present invention the base may be selected from the group consisting of sodium hydroxide, potassium hydroxide, sodium carbonate and potassium carbonate. Preferable basic solution is sodium hydroxide solution.

According to yet another aspect of the present invention, the purified donepezil maleate is suspended in a mixture of toluene and water. Aqueous NaOH is added and the phases are separated (donepezil base is dissolved in toluene). The organic phase containing the Donepezil base solution is washed with water and the phases are separated. An equimolar quantity of aqueous hydrochloric acid solution is added, and the phases are separated (donepezil HCl is dissolved in water). An inactive pharmaceutical ingredient is optionally added; the solution is stirred and then freeze-dried or spray-dried.

In yet another aspect, the present invention relates to stable, non-hygroscopic, substantially amorphous donepezil hydrochloride, per se or diluted, which can be used for solid dosage form formulations thereof. The active pharmaceutical ingredient may be diluted with pharmaceutically acceptable excipients.

In a preferred embodiment, the present invention provides a process for producing amorphous donepezil hydrochloride by lyophilization or spray-drying of an aqueous solution optionally containing a pharmaceutically inactive ingredient such as lactose.

As used herein, "amorphous" means a solid devoid of long-range crystalline order; "diluted amorphous" means an amorphous mixture of the active pharmaceutical ingredient with one or more additives, as described below.

According to yet another aspect of the present invention, the inactive pharmaceutical ingredients may be selected without limitation from the group consisting of cellulose derivatives such as hydroxypropylmethyl cellulose, hydroxypropyl cellulose, methyl cellulose, mono and disaccharides such as mannitol and lactose, starches and maltodextrins, or a mixture thereof. Preferably the additive is lactose and more preferably lactose monohydrate, which is a widely used inactive ingredient and known to be safe. Its good solubility in water makes it very suitable for formulations.

Still another feature of the invention is the wide range of the amount of the inactive/active ingredients used, apart from the possibility to use the invention without the addition of the inactive ingredient. This ratio can be anything from about 10/1 to 0.1/1. The product obtained is always suitable for making pharmaceutical formulations due to its good mechanical behavior and low hygroscopicity. The preferred inactive/active ingredients ratio is from about 6/1 to about 1/1, more preferably the inactive/active ingredients ratio is 3/1.

Although, the following examples illustrate the practice of the present invention in some of its embodiments, the examples should not be construed as limiting the scope of the invention. Other embodiments will be apparent to one skilled in the art from consideration of the specification and examples. It is intended that the specification, including the examples, is considered exemplary only, with the scope and spirit of the invention being indicated by the claims which follow.

EXAMPLES

HPLC measurements of donepezil maleate samples were performed using HPLC JASCO, LC-1500 series, equipped with Phenomenex Luna phenyl hexyl column, 5 µm, 250×4.6 mm, and a UV detector operated on 318 nm. Analyses were performed using the following mobile phase, at flow rate of 1.0 ml/minute, temperature of 40° C., and run time of 50 minutes.

Mobile phase:

Solution A: 940 ml WATER+50 ml THF+14 ml TEA, pH adjusted to 2.0 with $H_3PO_4$.

Solution B: 950 ml METHANOL+50 ml THF

Eluent A: 75% A+25%

Eluent B: 25% A+75% B

| Gradient table | | |
| --- | --- | --- |
| Time (min) | % Eluent A | % Eluent B |
| 0 | 100 | 0 |
| 20 | 100 | 0 |
| 30 | 0 | 100 |
| 50 | 0 | 100 |

Example 1

Preparation of Crude Donepezil Maleate

A solution of donepezil base (3.5 g) dissolved in toluene (42 ml), obtained as described in European patent application EP 1386607, was charged in a 500 ml flask. Water (22.5 ml) was added to afford a suspension and stirring was maintained for 15 minutes. The stirring was stopped to allow the two layers to settle for 15 minutes. The phases were separated and the organic layer was washed with water (22.5 ml). The mixture was stirred at 25°-30° C. and maleic acid (1.92 g) was added at same temperature. Upon completion of the addition, the donepezil maleate salt precipitated from the two-phase solution. Mixing was continued at 25° C. for 1 hour, and then the mixture was cooled to 5°-10° C. and mixing was continued at this temperature for 1 hour. The solid was obtained by filtrating out the liquid and the resulting cake was washed with cold water (2×10 ml) followed by cold acetone (2×10 ml). 3.9 g crude donepezil maleate was obtained in 90% yield (equivalent to 3.8 g of dry product) having purity of 99.4% (by HPLC) and melting point of 125-131° C.

Example 2

Preparation of Crude Donepezil Maleate

A solution of donepezil base (3.5 g) dissolved in toluene (42 ml), obtained as described in U.S. Pat. No. 6,252,081, is charged in a 500 ml flask. Water (22.5 ml) is added to afford a suspension and stirring is maintained for 15 minutes. The stirring is stopped to allow the two layers to settle for 15 minutes. The phases are separated and organic layer is washed with water (22.5 ml). The mixture is stirred at 25°-30° C. and maleic acid (1.92 g) is added at same temperature. Upon completion of the addition, the donepezil maleate salt precipitates from the two-phase solution. Mixing is continued at 25° C. for 1 hour, and then the mixture is cooled to 5°-10° C. and mixing is continued at this temperature for 1 hour. The solid is obtained by filtrating out the liquid and the resulting cake is washed with cold water (2×10 ml) followed by cold acetone (2×10 ml). 3.9 g crude donepezil maleate is obtained in 90% yield (equivalent to 3.8 g of dry product) having purity of 99.4% (by HPLC) and melting point of 125-131° C.

Example 3

Preparation of Crude Donepezil Maleate

A solution of donepezil base (3.5 g) dissolved in toluene (42 ml), obtained as described in patent WO 97/22584, is charged in a 500 ml flask. Water (22.5 ml) is added to afford a suspension and stirring is maintained for 15 minutes. The stirring is stopped to allow the two layers to settle for 15 minutes. The phases are separated and organic layer is washed with water (22.5 ml). The mixture is stirred at 25°-30° C. and maleic acid (1.92 g) is added at same temperature. Upon completion of the addition, the donepezil maleate salt precipitates from the two phase solution. Mixing is continued at 25° C. for 1 hour, and then the mixture is cooled to 5°-10° C. and mixing is continued at this temperature for 1 hour. The solid is obtained by filtering out the liquid and the resulting cake is washed with cold water (2×10 ml) followed by cold acetone (2×10 ml). 3.9 g crude donepezil maleate is obtained in 90% yield (equivalent to 3.8 g of dry product) having purity of 99.4% (by HPLC) and melting point of 125-131° C.

Example 4

Crystallization of Crude Donepezil Maleate

Wet crude donepezil maleate (4.6 g, equivalent to 4.0 g dry material) was charged in a 250 ml flask and acetone (60 ml) was added. The mixture was vigorously stirred and heated to reflux to afford a clear solution. The solution was cooled to 25° C. and the suspension was mixed at this temperature for 1 hour to afford crystallization. The mixture was then cooled to 5°-10° C. and stirring was continued at this temperature for additional 1 hour.

The solid was obtained by filtering out the liquid and the resulting cake was washed with cold acetone (2×5 ml). 3.8 g of wet crystallized donepezil maleate (equivalent to 3.2 g of dry product) was obtained in 80% yield having purity of 99.9% (by HPLC).

Example 5

Preparation of Donepezil Hydrochloride from Donepezil Maleate

Donepezil maleate (10.8 g) was suspended in toluene (80 ml) and water (70 ml) was added in a 500 ml flask. The mixture was stirred at room temperature and 47% sodium hydroxide solution was added. The solution was warmed to 35-40° C. and mixed at this temperature for 2 hours. The stirring was stopped to allow the two layers to settle for 15 minutes. The phases were separated and the pH of the aqueous phase was checked (The measured pH value was 11.6). The toluene solution containing donepezil base was washed with water (80 ml) and stirring was continued at room temperature for 30 minutes. The stirring was stopped to allow the two layers to settle for 15 minutes. The phases were separated and the pH of the aqueous phase was checked (The measured pH value was 7.7). An aliquot of 1.8 ml of the toluene solution was withdrawn and set aside. Water was added (160 ml) and the mixture was stirred with 1N HCl solution (17 ml, which corresponds to 85% of the calculated quantity) and stirring was continued for 15 minutes at room temperature. The pH of the aqueous phase was checked (The measured pH value was 5.4). The remaining 1N HCl solution (3 ml) was added in 0.5 ml increments followed by stirring for 5 minutes after each addition. Addition was ceased when pH was less than 5. Half of the donepezil base, which was set aside, was added to the toluene layer. Stirring was continued for 5 minutes at room temperature and second half of the donepezil base was added. Stirring was stopped to allow the layers to settle for 15 minutes and phases were separated. The aqueous solution containing donepezil hydrochloride was filtered through a 0.5μ filter to remove any insoluble matters and lactose monohydrate (15 g) was added to the aqueous solution, which was poured on a lyophilization tray and frozen at −50° C. for up to 4 hours and lyophilized under vacuum of 50 miliTorr for about 60 hours to obtain 8.0 g of pharmaceutically pure donepezil hydrochloride, in 88% yield.

What is claimed is:

1. A process for converting donepezil maleate to amorphous donepezil hydrochloride of pharmaceutical purity, comprising the steps of:
   suspending pure donepezil maleate in a mixture of an organic solvent and water;
   adding aqueous inorganic base;
   extracting and separating the aqueous phase from the organic phase;
   washing the organic phase with water and separating the aqueous phase from the organic phase;
   adding equimolar quantity of aqueous hydrochloric acid to the organic phase and separating the aqueous phase from the organic phase;
   optionally adding an inactive pharmaceutical ingredient to the aqueous phase and stirring to dissolution; and
   evaporating the water directly from the aqueous extraction phase by freeze drying or spray drying, to produce pharmaceutically pure amorphous donepezil hydrochloride.

2. The process according to claim 1, wherein the organic solvent is selected from the group consisting of dichloromethane, chloroform, ethyl acetate, isopropyl acetate, isobutyl acetate, xylenes, and toluene, or a mixture thereof.

3. The process according to claim 2, wherein the organic solvent is toluene.

4. The process according to claim 1, wherein the aqueous inorganic basic solution is selected from the group consisting of sodium hydroxide, potassium hydroxide, potassium carbonate, and sodium carbonate solutions.

5. The process according to claim 4, wherein the basic inorganic solution is a sodium hydroxide solution.

6. The process according to claim 1, wherein the inactive pharmaceutical ingredient is selected from the group consisting of cellulose derivatives, wherein such cellulose derivatives are hydroxypropylmethyl cellulose, hydroxypropyl 1 cellulose, methyl cellulose, mono and disaccharides, wherein such mono and disaccharides are mannitol and lactose, starches and maltodextrins, or a mixture thereof.

7. The process according to claim 6, wherein the inactive ingredient is lactose.

* * * * *